United States Patent [19]

D'Antonio

[11] Patent Number: 5,318,522
[45] Date of Patent: *Jun. 7, 1994

[54] HYPODERMIC FLUID DISPENSER

[76] Inventor: Nicholas F. D'Antonio, 7695 Admiral Dr., Liverpool, N.Y. 13090

[*] Notice: The portion of the term of this patent subsequent to Jan. 14, 2009 has been disclaimed.

[21] Appl. No.: 818,235

[22] Filed: Jan. 8, 1992

Related U.S. Application Data

[63] Continuation-in-part of Ser. No. 336,636, Apr. 7, 1989, Pat. No. 5,080,648, which is a continuation of Ser. No. 59,620, Jun. 8, 1987, abandoned.

[51] Int. Cl.$^5$ ............................................. A61M 11/00
[52] U.S. Cl. ......................................... 604/72; 604/71; 604/135
[58] Field of Search ................. 604/67, 71, 72, 134, 604/135, 151, 153-155, 62

[56] References Cited

U.S. PATENT DOCUMENTS

| | | | |
|---|---|---|---|
| 1,880,354 | 7/1931 | Mueller | 604/134 |
| 2,675,802 | 4/1954 | Hein | 604/68 |
| 2,762,369 | 9/1956 | Venditty | 604/68 |
| 2,800,903 | 7/1957 | Smoot | 604/68 |
| 3,134,380 | 5/1964 | Armao | 604/198 |
| 3,136,313 | 6/1964 | Enstrom et al. | 604/139 |
| 3,138,157 | 6/1964 | Ziherl et al. | 604/71 |
| 3,262,449 | 7/1966 | Pannier et al. | |
| 3,419,007 | 12/1968 | Love | 604/72 |
| 3,490,451 | 1/1970 | Yahner | |
| 3,526,225 | 9/1970 | Isobe | |
| 3,557,784 | 1/1971 | Shields | 604/68 |
| 3,649,299 | 3/1972 | Sholl | |
| 3,985,535 | 10/1976 | Bennett et al. | |
| 4,014,206 | 3/1977 | Taylor | 604/122 |
| 4,059,107 | 11/1977 | Iriguchi et al. | |
| 4,103,684 | 8/1978 | Ismach | |
| 4,396,384 | 8/1983 | Dettbarn et al. | |
| 4,400,171 | 8/1983 | Dettbarn et al. | 604/68 |
| 4,410,323 | 10/1983 | Hodosh et al. | 604/212 |
| 4,413,991 | 11/1983 | Schmitz et al. | 604/191 |
| 4,416,663 | 11/1983 | Hall | 604/198 |
| 4,424,057 | 1/1984 | House | 604/88 |
| 4,518,385 | 5/1985 | Lindmayer et al. | |
| 4,529,401 | 7/1985 | Leslie et al. | 128/DIG. 1 |
| 4,552,277 | 11/1985 | Richardson et al. | 604/411 |
| 4,592,742 | 6/1986 | Landau | 604/71 |
| 4,623,332 | 11/1986 | Lindmayer et al. | 604/68 |
| 4,668,220 | 5/1987 | Hawrylenko | 604/155 |
| 4,687,465 | 8/1987 | Prindle et al. | 604/62 |
| 4,752,267 | 2/1988 | Vailcancourt | 604/198 |
| 4,753,638 | 6/1988 | Peters | 604/212 |
| 4,784,640 | 11/1988 | Johnson et al. | 604/62 |

FOREIGN PATENT DOCUMENTS 0087314  8/1959  Denmark ............................ 604/134

OTHER PUBLICATIONS

*Mode of Operation of the Compressor in a Jet Injector*, Meditsinskaya Tekhniko, vol. 11, No. 1, pp. 23–27, Jan.–Feb. 1977.

*Comparative Evaluation of Three Jet Injectors for Mass Immunization*, Canadian Journal of Public Health, vol. 68, pp. 513–516, Nov.–Dec. 1977.

*Efficacy of an Absorbed Trivalent Split Influenza Vaccine Administered by Intradermal Route*, Arch. Roum. Path., Exp. Microbiol. T. 40, No. 1, pp. 67–70, Jan.–Mar. 1981.

Primary Examiner—Ralph Lewis
Attorney, Agent, or Firm—D. Peter Hochberg; Mark Kusner; Michael Jaffe

[57] ABSTRACT

A hypodermic fluid dispenser and collapsible cartridges having fluid-holding chambers therefor includes an insertor device for moving the cartridges into the dispenser, a resilient device for collapsing the cartridges, a motor energizing the resilient device and a source of electrical energy for the motor.

36 Claims, 11 Drawing Sheets

Fig. 4
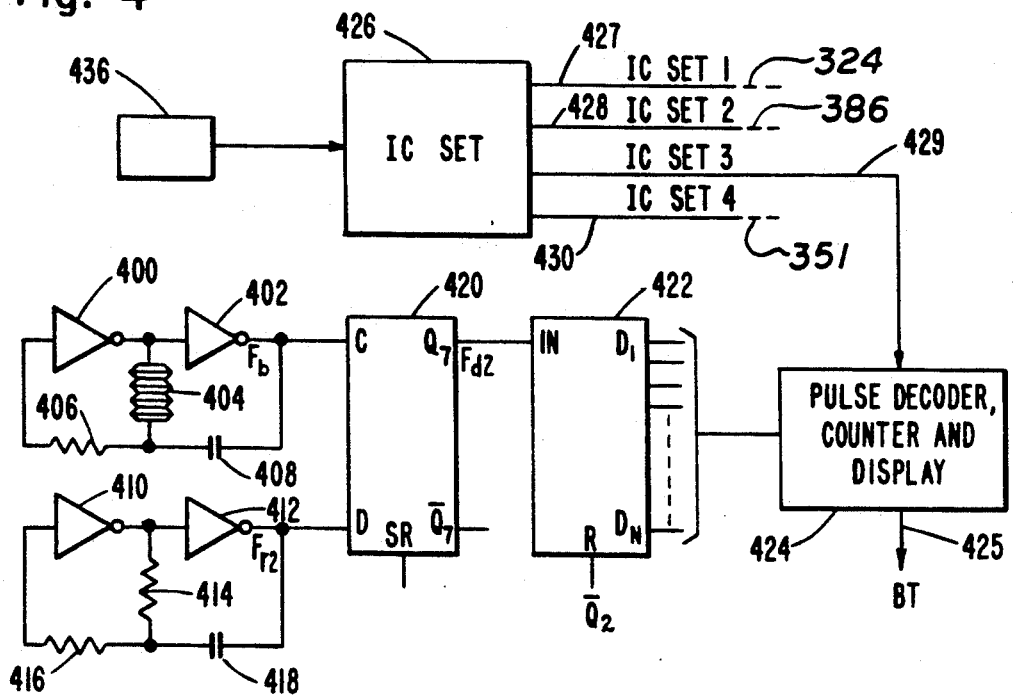
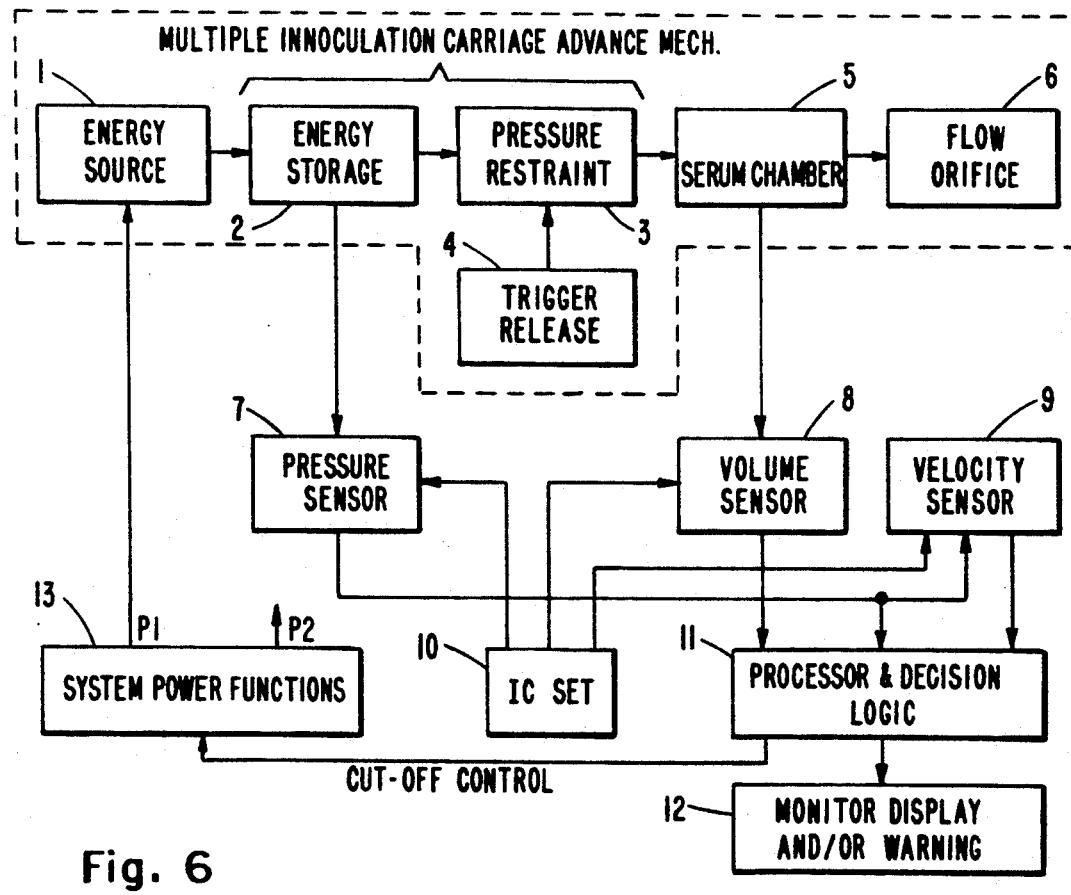
Fig. 6

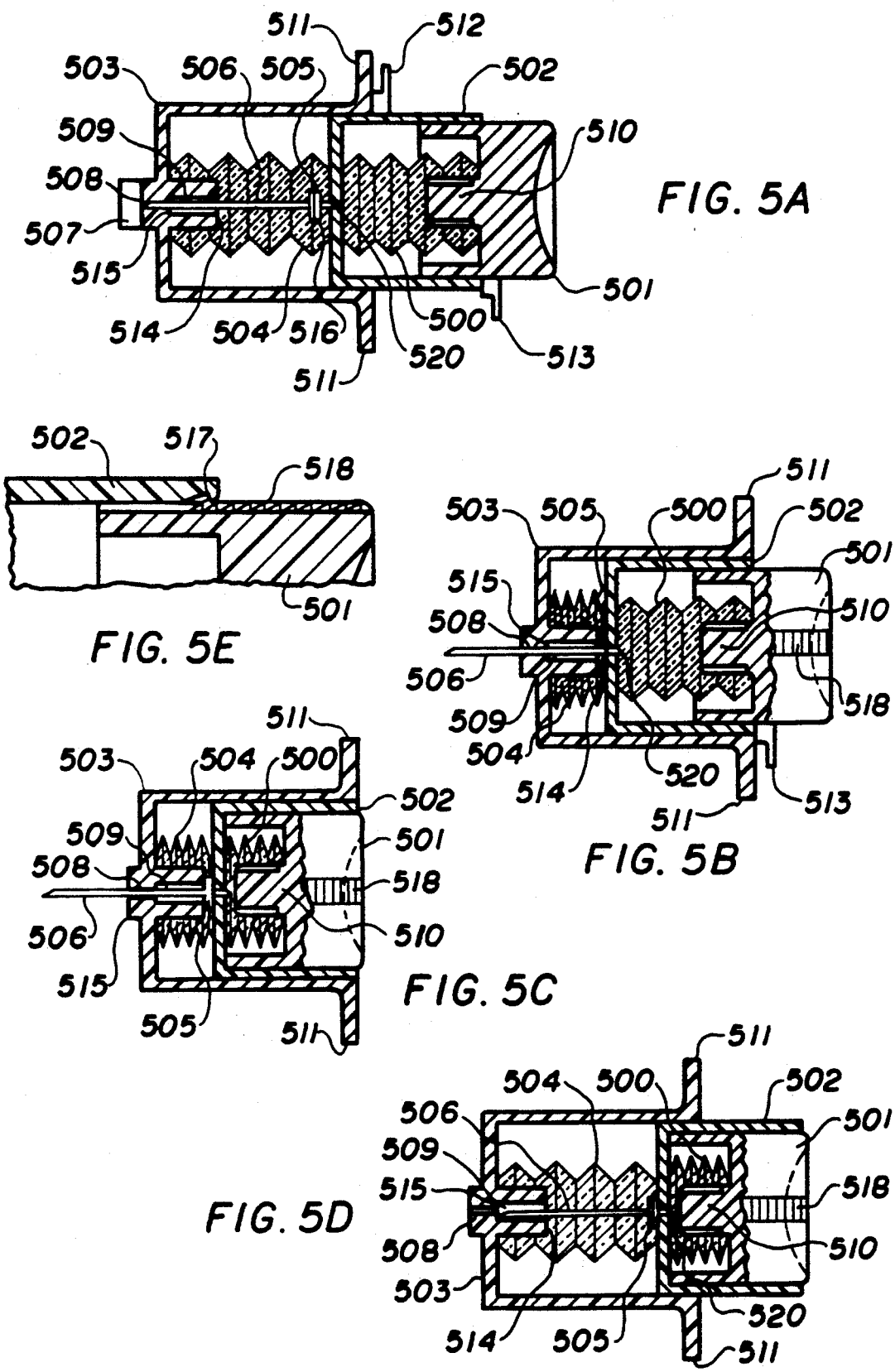

HYPODERMIC FLUID DISPENSER

CROSS-REFERENCE TO RELATED APPLICATION

This application is a continuation-in-part of corresponding U.S. patent application Ser. No. 07/336,636, filed Apr. 7, 1989; now U.S. Pat. No. 5,080,648 which is a file wrapper continuation of U.S. Ser. No. 07/059,620, filed Jun. 8, 1987, now abandoned.

TECHNICAL FIELD

This invention relates to apparatus for the hypodermic injection of fluids.

BACKGROUND OF THE INVENTION

Hypodermic fluid dispensers fall into two broad categories, namely, needle hypodermic dispensers and jet injectors. Jet injectors are particularly useful in immunization programs which involve the delivery of a non-living virus; and needle injectors are useful in the delivery of non-living virus and of medications.

In general, jet inoculation, as compared to needle inoculation, is less traumatic, presents a lower risk of cross-contamination, requires less operator training, and allows a higher number of procedures per unit of time.

Although both needle hypodermic injectors and high pressure jet injectors have been widely used, the presently known devices have serious disadvantages. The problems associated with needle injectors in the spread of AIDS (Acquired Immune Deficiency Syndrome) alone is sufficient motivation to avoid proliferation of today's needle systems. People cannot be relied upon to dispose of needle injectors in accordance with instructions and good practice; and an element of the population are tempted to reuse needles without knowledge of or regard for safe practices.

Jet injectors generally avoid the above-referenced problems associated with needle injectors; however, the presently available injectors are expensive; prone to failure; too bulky to transport conveniently; and are generally inconvenient to use.

DISCLOSURE OF THE INVENTION

In accordance with the preferred embodiment of the present invention, a hypodermic fluid dispenser comprises insertion means for inserting one or more collapsible bodies each having a fluid chamber, pressure application means including a resilient device for collapsing the bodies, and motor means with an appropriate source for energizing the resilient means.

Advantageously, my invention is applicable to both needle injectors and high pressure jet hypodermic injectors.

BRIEF DESCRIPTION OF THE DRAWINGS

The invention is illustrated in the accompanying drawing in which:

FIG. 3 and FIG. 4 are schematic representations of one embodiment of the control, monitoring, and motor drive circuitry of the jet injector system of FIGS. 2 or 7;

FIGS. 5A through 5E illustrate side, cross-sectional views of a needle hypodermic injector in accordance with my invention in a sequence of stages which occur in use of the injector;

FIG. 6 is a block diagram overview of a multiple inoculation jet injector system in accordance with my invention;

DETAILED DESCRIPTION OF THE EMBODIMENTS

Figure 1:
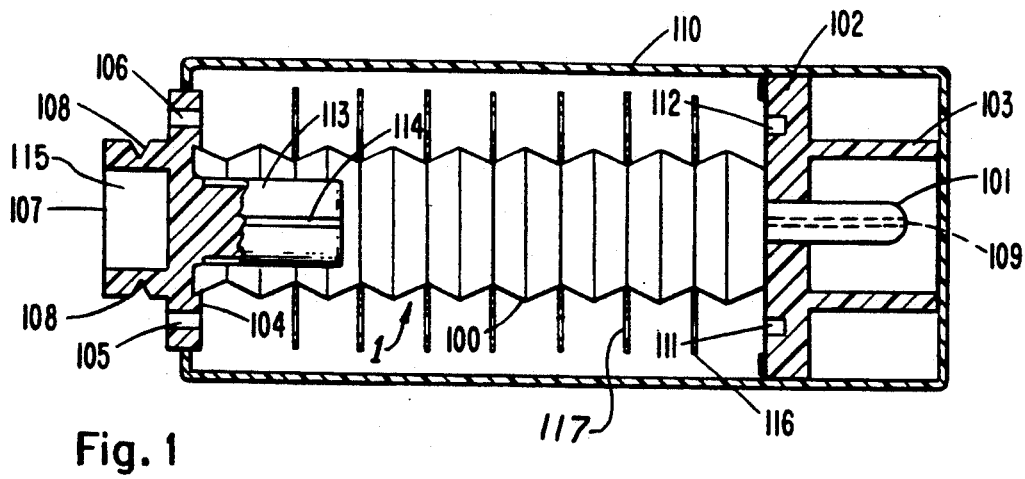
FIGS. 1 and 1A illustrate side, cross-sectional views of two multiple inoculation jet injectors in accordance with the invention.

FIG. 1 illustrates a liquid filler jet injector or dispenser 1 stored in a protective cover 110. The jet injector of FIG. 1 comprises a liquid-filled bellows 100; a front plate 102 which comprises a pair of guide rod recesses 111 and 112, a set of thin washers 116 which have an inner diameter slightly larger than the minor diameter of bellows 100, a pair of holes 117 in each of the washers 116 that are aligned with the guide rod recesses 111 and 112 and with the openings 105 and 106; a spacing guard ring 103, with an interrupted pattern 901 shown in FIG. 1B to prevent sliding between the dispenser and the skin; a disposable and replaceable exit nozzle 101 with an output port 109 (shown in greater detail in FIG. 1C); a ram 113 with a groove 114; and a back plate 104. Guard ring 103 can advantageously have the features shown in FIGS. 1B and 1C, respectively. An interrupted pattern 901 at the end of ring 103 in FIG. 1B prevents sliding between the dispenser and the skin of the person being injected. The nozzle 101 has its end 903 threaded in FIG. 1C or the like so that it can be disposable and replaced. The back plate 104 comprises openings 105 and 106, aligned with holes 117 in washers 116, which accept a pair of guide rods when the jet injector cartridge is installed in the system of FIGS. 2A and 2B; and a ring 115 which forms the recess 107 for receiving a drive spring 227 of the system of FIG. 2A. The injector of FIG. 1 may be a disposable injector or a permanent reusable injector and the output port made of ceramic, plastic, glass or metal may be removable and replaceable or a permanent part of the bellows. In either case, device economy is improved by fabricating a molded output port having the flow orifice formed by first inserting a preformed metal, or other sufficiently sturdy member, whose size and shape, i.e., length, diameter and flow path angulation are chosen to provide laminar flow. Some of the other possible methods for forming the orifice include laser boring, water jet cutting and electron beam cutting.

Figure 2A:
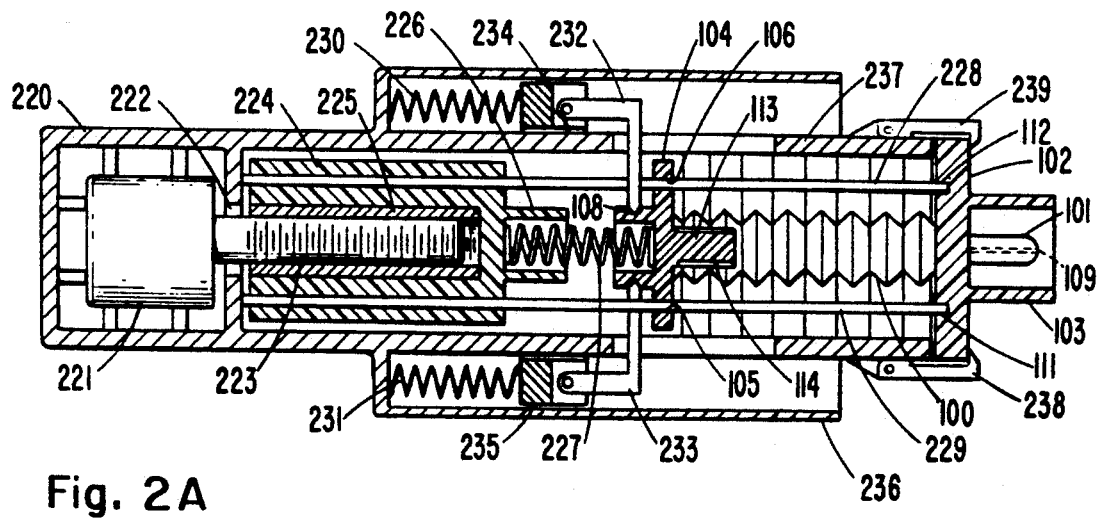
FIGS. 2A and 2AA illustrate cross-sectional views of jet injector systems with the fresh injectors of FIGS. 1 and 1A, respectively, installed therein.

FIG. 2A is a cross-sectional representation of an illustrative embodiment of a hypodermic jet injector system with a fresh jet injector of FIG. 1 installed therein. The system of FIG. 2 in general comprises: a housing 220; the control, monitoring and display arrangements of FIGS. 3 and 4 (not shown in FIG. 2A); a battery operated drive motor 221; a motor output shaft 222 with a threaded portion 223; a loading ram 224 with internal threads 225 which mate with the threads 223; an energy storage spring 227; a reluctance transducer shield 226 to be described with respect to FIG. 3 later herein; a pair of guide rods 228 and 229 that serve to align and support the bellows 100; retaining latches 238 and 239; and a trigger mechanism which comprises the detents 232 and 233, the follower springs 230 and 231 and the follower blocks 234 and 235. The mechanism for releasing the detents 232 and 233 is not shown in FIG. 2 and any suitable mechanical linkage which effects the simultaneous lifting of the detents 232 and 233 is satisfactory. In an alternative mechanical embodiment for loading energy storage spring 227, threaded motor shaft 222 is replaced with a shaft driven cam which serves to compress energy storage spring 227 as the motor shaft rotates.

Figure 2B:
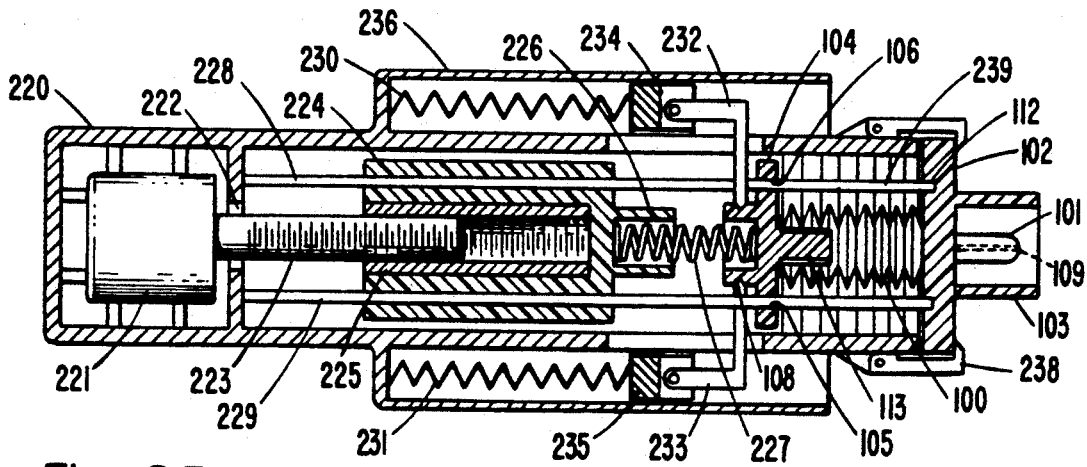
FIGS. 2B and 2BB illustrate side, cross-sectional views of the jet injector systems of FIGS. 2A and 2AA, respectively, with the injectors partially expended.
Figure 1A:
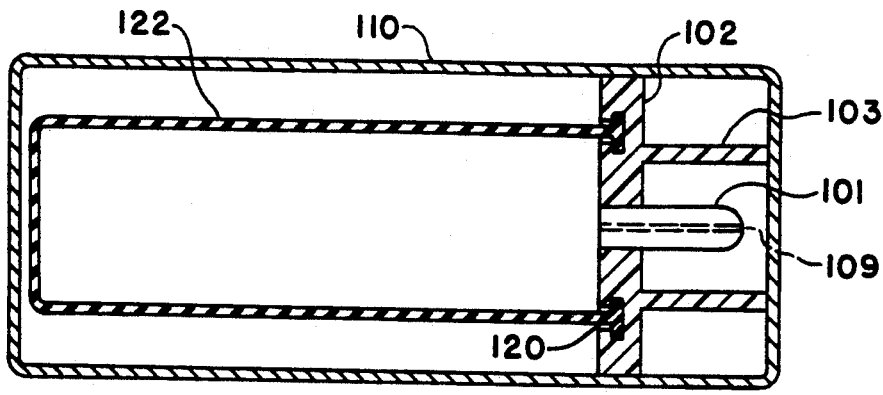
Figure 2A:
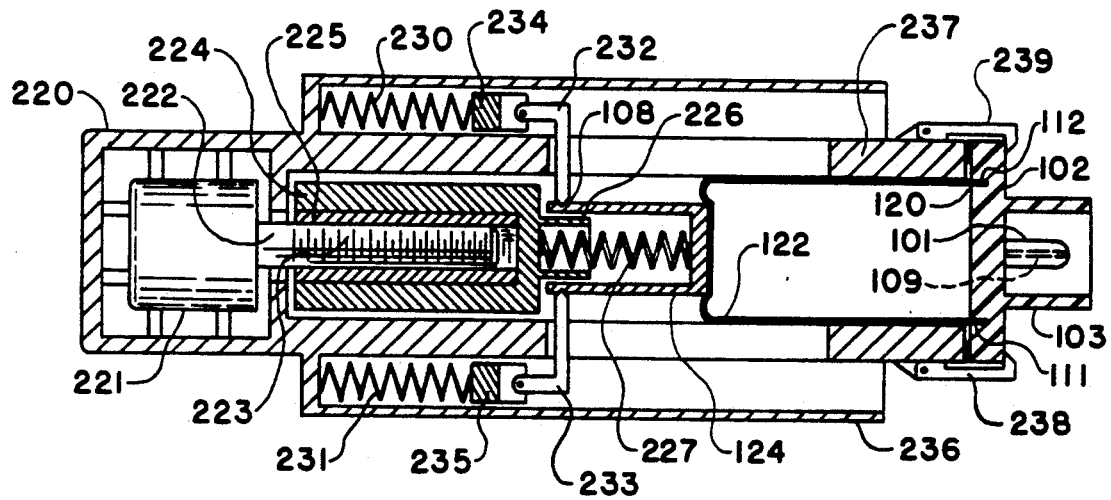
Figure 2B:
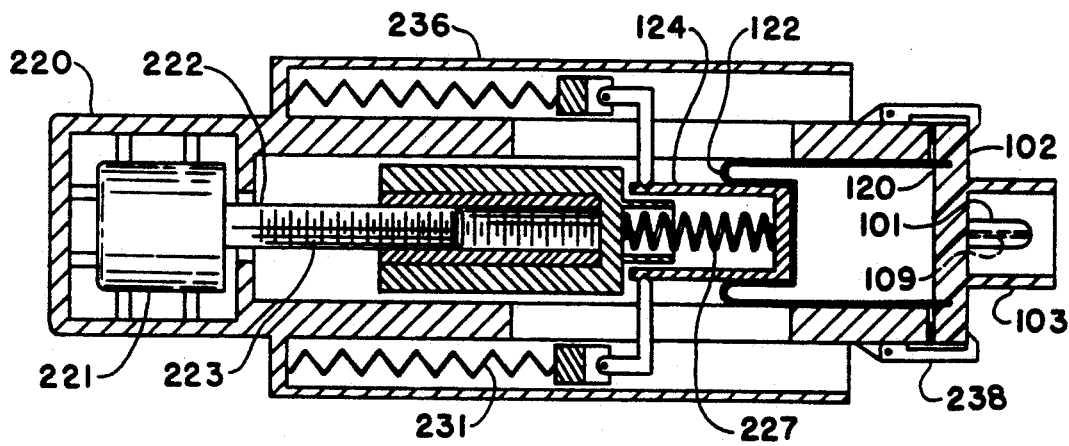
Figure 1B:
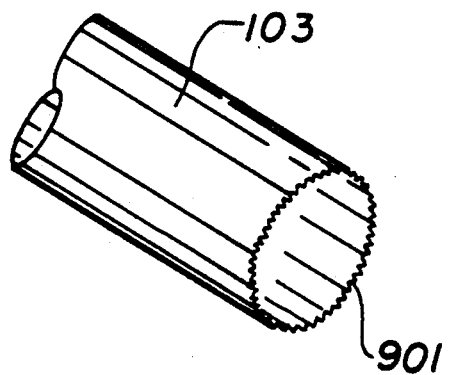
FIG. 1B is a partial pictorial view of a modified body ring guard for use in the injectors of FIGS. 1 and 1A.
Figure 1C:
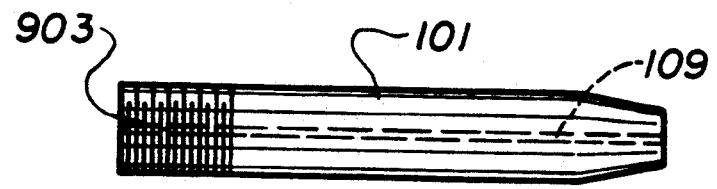
FIG. 1C is a pictorial view of a modified nozzle for use in the injectors of FIGS. 1A and 1B.

An alternate embodiment of the injector of FIGS. 1, 2A and 2B is illustrated in FIGS. 1A, 2AA, and 2BB. In the alternate embodiment, the liquid-filled bellows 100 is replaced by a collapsible liquid-filled "hat" diaphragm-type structure. Detents 111 and 112 of FIG. 1 are replaced in FIG. 1A by slot 120 for mounting and firmly securing hat structure 122 to the front plate 102. This arrangement is equally effective if the fluid chamber is replaced by a piston-type syringe.

FIG. 2AA is a cross-sectional representation of the injector system with a fresh injector installed therein. When the diaphragm 122 is inserted in the now conformal housing 220, a slight initial collapse of 122 occurs to facilitate chamber venting and to assure an effective inner folding action as the multiple injections follow. The conformal shape of housing 220 constrains fluid chamber 122 and thus prevents undesired outward expansion under the influence of the injection pressure when the spring 227 is released. Back plate 124 is configured to assure that the detents 232 and 233 do not interfere with fluid chamber 122 as it progressively folds inside its outside diameter (FIG. 2BB) with each additional injection. In the case of the syringe, the piston is progressively pushed to the right as the injections occur.

While the following discussion is specific to the embodiment of FIGS. 1, 2A and 2B, the discussion applies equally to the alternate embodiment of FIGS. 1A, 2AA and 2BB and the piston-type syringe dispenser.

Prior to the time that a fresh jet injector of FIG. 1 is installed in the system of FIG. 2, a manually operable reset switch 436 of FIG. 4 is operated to enable the IC Set circuit 426 of FIG. 4 to establish initial system conditions. Output signals of the circuit 426 sends signal 430 to enable motor reset 351 of FIG. 3 to draw the loading ram 224 back into the initial position illustrated in FIG. 2A or to rotate the cam to its starting position, signal 427 to initialize the digital pulse decoder 324, signal 428 for the digital window decoder 386 and signal 429 to the pulse decoder, counter, and display 424. Alternatively, the ram 224 or the cam can be manually returned to the initial position at the time that a fresh bellows is installed.

The functions of the pulse decoder 324, the window decoder 386 and the pulse decoder counter and display 424 will be apparent from the description of FIGS. 3 and 4 which appears later herein. After the system is thus conditioned, a fresh jet injector is removed from the protective cover 110 and inserted into the housing 220 as illustrated in FIG. 2A. To install the jet injector, the guide rods 228 and 229 are inserted into the openings 105 and 106 in the back plate 104, through the openings 117 in the washers 116, and the injector is moved into the housing 220 until the front face of the front plate 102 is clamped by the latches 238 and 239. As the jet injector is moved into the housing 220, the detents 232 and 233 engage the notches 108 in the back plate 104 and follow the motion of the back plate as it is moved to the left in FIG. 2A. The follower blocks 234 and 235 follow the motion of the detents 232 and 233 to the left and thus compress the follower coil springs 230 and 231. Further, when a fresh injector is in position as illustrated in FIG. 2A, the energy storage spring 227 enters the recess 107 in the back side of the back plate 104. The system of FIG. 2A is in condition for an operator to perform a series of inoculations.

Figure 3:
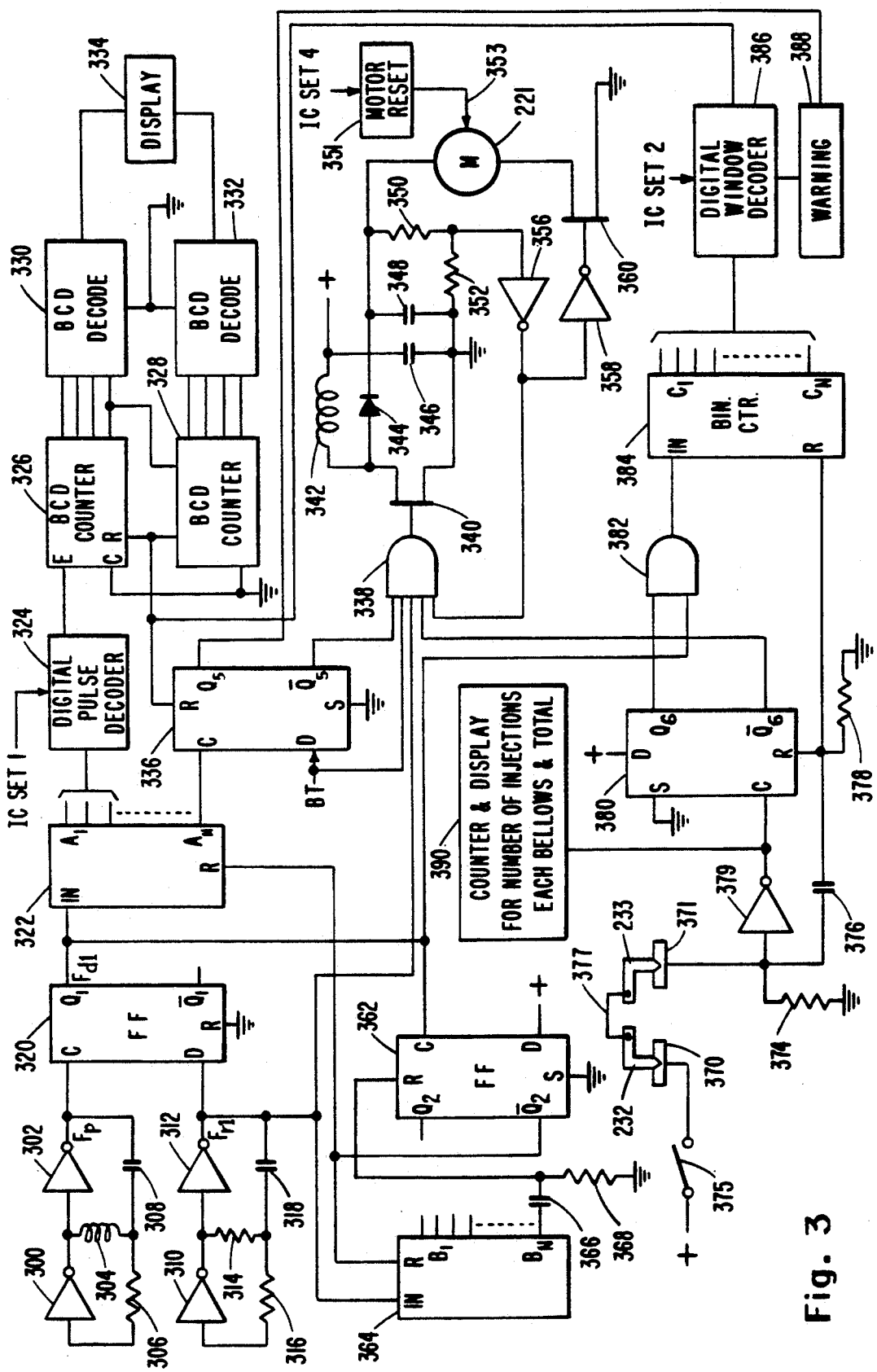

Under operator control, the system of FIGS. 2A, 3 and 4 selectively provides power to the motor 221 to advance the ram 224 to the right in FIG. 2A and thus compress the coil spring 227. As described later herein, the circuitry of FIG. 3 monitors the degree of compression of the spring 227 and removes power from the motor when the compression reaches a target value. The target value is either a default value established by the manufacturer or a value established by an operator on the basis of experience. After the spring has been compressed to the target value, the guard 103 is held perpendicular to and against the skin at a suitable site of a subject to be injected. The outer ring surface of guard 103 may have a tooth-like pattern 901 to reduce the possibility of the ring sliding along the skin during the course of an injection. If the ring does slide during the injection the subject may receive a "jet cut" rather than a jet inoculation. The operator initiates injection by depressing a trigger, which as indicated earlier herein is not shown in the drawing. Depression of the trigger simultaneously releases the detents 232 and 233 from the recesses 108 in the back plate 104. The energy stored in the spring 227 is released and the back plate 104 is rapidly driven to partially collapse the bellows 100. As the bellows is collapsed, a desired amount of fluid is driven through the output port 109 in the projection 101. Advantageously, the use of a compressed spring as a source of energy provides a high initial pressure which reduces as the bellows 100 collapses. The size and the length of the port 109 and the pressure profile supplied by the compressed spring projects the fluid with a desired pressure profile which assures hypodermic injection of the fluid to the desired depth. The diameter and the length of the port 109 are chosen to assure laminar flow of the fluid from the chamber to the output tip. As the bellows collapse, guide washers 116 move together and prevent the bellows from bending under the influence of the high initial force of the injection.

As explained earlier herein, when a fresh injector is inserted into the housing 220, the follower springs 230 and 231 are compressed. Therefore, after the trigger is released, the follower blocks 234 and 235 and the detents 232 and 233 are driven to the right in FIG. 2A until the detents again engage the corresponding recesses 108 in the back plate 104. The follower blocks 234 and 235 may be connected to a small dashpot if a delay in this action is desired. The system of FIG. 2A is then again ready for the operator to initiate another injection.

Because the wall of the bellows 100 has a finite thickness, a fully collapsed bellows has a substantial length. The length of the ram 113 approximates the length of the collapsed bellows. Without the ram 113, valuable fluid is left in a fully collapsed bellows. The groove 114 in the ram 113 prevents the trapping of fluid in the portions of the bellows which surround the ram 113.

The above description is a general outline of the inoculation process with detailed reference to the control, monitoring, motor drive and display apparatus of FIGS. 3 and 4. While it is my intent to provide safe, low cost and convenient-to-use hypodermic injectors, I also provide measures of electronic monitoring, motor drive and control not found in known jet injectors.

FIG. 6 provides a block diagram functional overview of a hypodermic jet injector system in accordance with my invention. The dotted line of FIG. 6 provides a logical division between the mechanical portions of the injector system and the electronic monitoring, motor drive and control portions of the system.

The functional boxes 1 through 6 of FIG. 6 correspond to elements of the illustrative embodiment of FIGS. 2A and 2B as follows:

| FIG. 6 | FIG. 2A |
| --- | --- |
| Energy Source 1 | Motor 221 |
| Mechanical Energy Storage 2 | Spring 227 |
| Pressure Restraint 3 | Detents 232 and 233 |
| Trigger Release 4 | Not shown in drawing |
| Serum Chamber 5 | Jet injector of FIG. 1 including Bellows 100 |
| Flow Orifice 6 | Output Port 109 |

Although the illustrative embodiment of FIG. 2A employs a battery-operated geared down motor 221 to compress the coil spring 227, this requirement can be fulfilled by a variety of manual arrangements utilizing gears or other means of mechanical advantage. While the spring is preferred for storing mechanical energy, the blocks 1 and 2 of FIG. 6 could be replaced by other arrangements, e.g., a powerful solenoid, gas or hydraulic pressure. The critical requirement of the blocks 1 and 2 is that the serum chamber 100 receives enough force for a sufficient period of time to assure an effective inoculation.

The monitoring functions of FIG. 6 inform an operator when the device is ready to perform an injection, i.e., all system parameters are within acceptable limits of performance. A warning is issued when performance is not within limits and the system is disabled in the event of a malfunction.

The pressure sensor 7 of FIG. 6 monitors the status of the energy storage device 2 and compares the magnitude of the stored energy to a target magnitude. When the magnitude of the energy stored reaches the target value, the storage of energy is terminated. The target value may be a default value established by the manufacturer or a value established by the operator on the basis of experience with different subjects, e.g., adults, children, animals, and/or types of serum. DNA technology, agricultural procedures and different types of serum may be better served with different pressures. The target pressure value is one of the "initial conditions" which an operator may set by controls in the IC Set function 10 of FIG. 6.

The volume sensor 8 provides assurance that a correct amount of liquid is used in each injection.

The velocity sensor 9 of FIG. 6 determines the time required for the stored energy to decay to some predetermined value after an injection. The decay time is a measure of output port performance. If the output port is partially clogged, the pressure decays too slowly; and if the output port is worn or too large, the pressure decays too rapidly. If a failure is detected, a warning will be issued to the operator and the system is disabled until corrective action is taken.

The IC Set 10 of FIG. 6 permits an operator to select initial condition values for the pressure sensor 7, the volume sensor 8 and the velocity sensor 9.

The processor and decision logic 11 issues control signals to the system power control 13 and status signals to the monitor display and warning unit 12.

In addition to the control and monitoring function described above herein, the circuit arrangements of FIG. 4 maintain a record of the number of injections completed or, in the case of the cartridge system described below in relation of FIGS. 7A and 7B, the number of cartridges remaining as the cartridges in the magazine are used up.

The implementation of the system functions by the arrangements of FIGS. 3 and 4 will be understood from the following description.

Digital inverters 310 and 312, resistors 314 and 316, and capacitor 318 are configured to form a reference frequency oscillator. The operating frequency $F_{r1}$ is determined by the time constant of the resistor 314 and the capacitor 318.

Digital inverters 300 and 302, capacitor 308, and variable sensing inductance 304 in FIG. 3 form a variable frequency reluctance transducer oscillator which has an operating frequency $F_p$. The operating frequency of the oscillator varies as a function of the value of the inductance in coil 304. The coil 304, which is not shown in FIG. 2A, is mounted at the center of recess 107 and inside the energy storage spring 227 and is partially covered by the reluctance shield 226 of FIG. 2A. It is noted that reluctance shield 226 is shown to the outside of spring 227 for illustrative clarity, however, it is ideally situated at the inside diameter of spring 227, which is quite large in order to develop 1700 psi or more as needed for an effective deep penetration injection. In any event, a change in the relative position of the coil 304 and the shield 226 as the spring 227 is compressed changes the inductance of the coil 304. Accordingly the frequency of the oscillator, which is determined by the time constant of the inductance of coil 304 and the capacitor 308, is determined by the degree of compression of the spring 227. It is noted that other types of oscillator networks can also be used for these functions, for example, analog comparators or amplifiers.

Flip flop 320 is configured as a frequency mixer which provides a digital output signal which has a pulse rate $F_{d1}$ which is the difference between the reference pulse rate $F_{r1}$ and the oscillator frequency $F_p$. In the absence of pressure on the spring 227, the frequencies $F_{r1}$ and $F_p$ are equal and the pulse rate $F_{d1}$ at the "1" output of flip flop 320 is zero.

In the illustrative embodiment of FIG. 3, energy enhancement techniques drive motor 221 with a series of high speed, high energy and relatively high voltage pulses. The output of AND gate 338 controls the generation of the motor drive pulses. The inputs to the AND gate 338 comprise: the "0" output of the flip flop 336 which remains high until the target value of spring compression is reached; the BT conductor from pulse decoder 424; the "0" output of the flip flop 380, which is high except when the trigger is activated to initiate an injection; the output of the inverter 356, which is high until the charge on capacitor 348 reaches a critical value; and the output conductor of the reference oscillator. When enabled, the output signal of AND gate 338 turns the FET 340 on and off at the rate $F_{r1}$ of the reference oscillator. When the transistor 340 is on, current will flow from positive potential through inductance 342 and the transistor 340 to ground. When the transistor 340 is subsequently turned off, the energy stored in the magnetic field of coil 342 will discharge through the path which is comprised of diode 344 and capacitor 348. The resistors 350 and 352 are of relatively high value; therefore, very little energy is lost in the path to ground through those two resistors. The magnitude of the voltage generated by the collapse of the magnetic field of coil 342 is very high and is dictated by the rate of collapse of the field. The rate of collapse is determined by the impedance of the discharge path. The diode 344 prevents reverse flow of current due to the buildup of voltage on the capacitor 348. Capacitor 346 is a stabilizing capacitor which provides an extra measure of current for the coil. 342 during the ON state of transistor 340. When the charge and corresponding voltage on capacitor 348 reaches a predetermined value the output of the threshold detector 356 will go low and gate 338 is disabled. The predetermined value represents a charge and voltage large enough to advance the motor 221. When the output of detector 356 goes low, the output of inverter 358 goes high to enable transistor 360 to provide a path for discharging the capacitor 348 through the winding of motor 221. As the charge is depleted and the voltage on the capacitor falls below the threshold value of detector 356, the output of detector 356 goes high to enable gate 340 to initiate another cycle of charging capacitor 348; and the output of inverter 358 goes low to disable transistor 360. High speed charging cycles will continue until the flip flop 336 is set to the "1" state which indicates that the energy stored in spring 227 has reached the target value. In the drawing, the output labeled $Q_5$ is the "1" output of the flip flop 336 and the complement output is termed the "0" output herein.

Figure 3A:
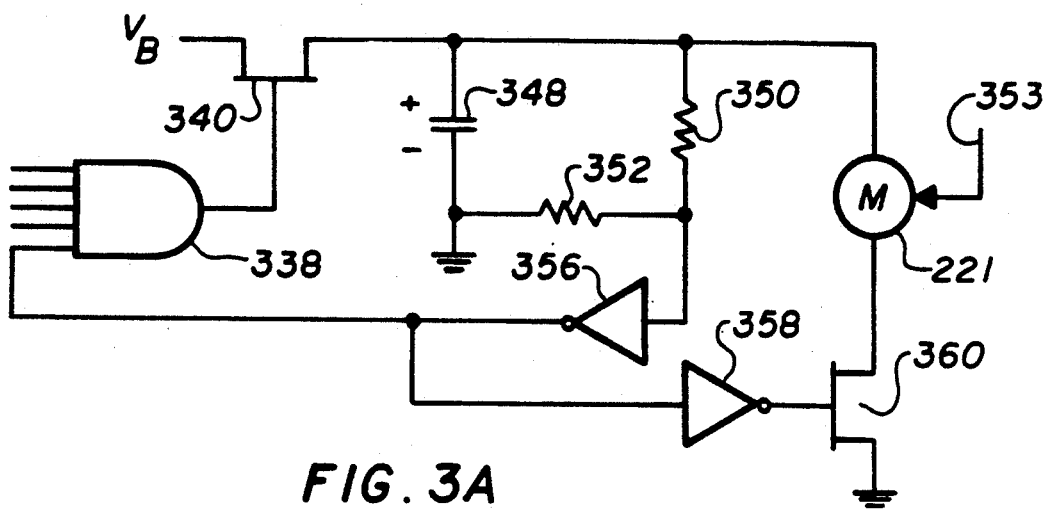
FIGS. 3A and 3B are schematic representations of alternative embodiments for the motor drive circuitry in the jet injector system of FIGS. 2 and 7.

The energy enhancement technique of the FIG. 3 embodiment allows for a power source that has neither the voltage or current capability for directly driving the motor. However, if the power source has a voltage level that satisfies that of the motor, but whose electrical current capability is insufficient, then the drive embodiment of FIG. 3A can be used. In this case, energy enhancement still applies, but the voltage amplification provided by coil 342 and diode 344 are eliminated and the corresponding loss in efficiency is eliminated as well. Instead, when all conditions for an injection are satisfied, gate 338 activates transistor 340 so that capacitor 348 is charged to the voltage level of the battery; that is, the mid-point of divider 350/352 is adjusted so that Schmitt trigger logic inverter 356 will change state when battery voltage is achieved on capacitor 348, and immediately thereafter, the motor is driven with closure of transistor 360 as described for the FIG. 3 embodiment. This scenario provides a high speed, high energy, albeit lower voltage, sequence of drive pulses to the motor. Capacitor 348 is selected to provide sufficient electrical current for a long enough time to exceed the design value for motor advancement.

Figure 3B:
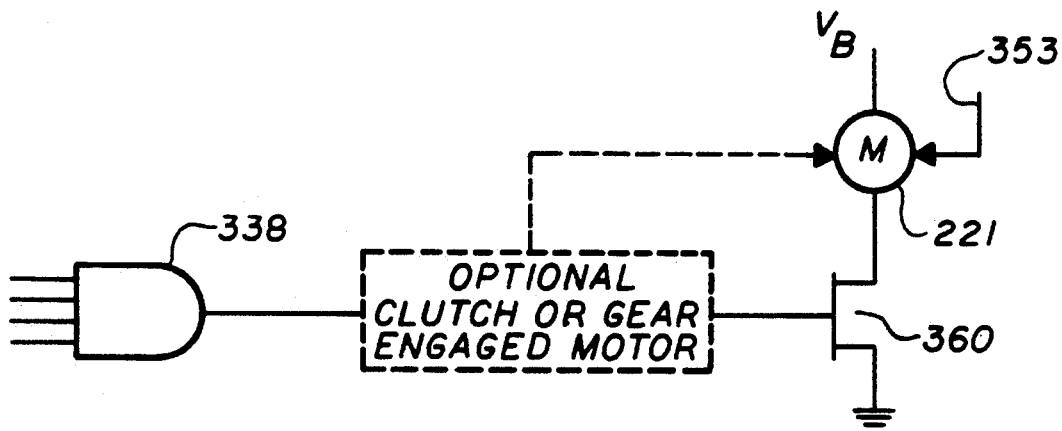

FIG. 3B shows an embodiment whose power source has enough instantaneous energy to drive the motor directly, i.e., one with enough current and voltage capability for driving the motor with no energy enhancement at all. In this case, transistor 340, coil 342, diode 344, capacitors 346 and 348, divider 350/352 and Schmitt inverters 356 and 358 are all eliminated. With this embodiment, the output of gate 338 will now drive transistor 360 so that the motor is connected directly to the power source when all conditions for an injection are met. A prototype of the "direct drive" system with a 9 volt alkaline battery achieved more than 400 injections in excess of 1700 psi each. With this arrangement, load time per injection is only 10 seconds; however, load time can be increased or decreased with variations in motor size, gear ratio, power capability and/or target pressure. It is also noted that for the same system, over 1,000 injections are achieved when using a higher energy density lithium battery.

While all of the jet systems described herein are smaller, lighter in weight and more convenient to use than those of the past, the selection of one drive technique as opposed to another is dictated by economics, acceptable load time and the primary use for the injector. For example, the FIG. 3 approach is the most compact because the total energy enhancement described will allow for a smaller motor/battery combination, however, it is also the least efficient and will result in fewer "shots" for a given amount of initial energy. A good example for this system is its daily use by diabetics where load time is not so critical and where it is easily carried in a woman's purse or a gentleman's pocket. When the maximum number of injections is paramount, such as mass immunization by the military, veterinary, DNA or agricultural procedures, then a better choice is the other end of the spectrum as shown in FIG. 3B, that is, using a larger, direct drive motor, with lower voltage, higher efficiency and faster load time.

Finally, because of the wide adaptability of the inventive system, some applications might use motors with very high start-up current and/or free-Wheeling rotors. If this is the case, the motor is ideally driven with an optional, electrically driven, clutch or gear engagement. In this way, the inertia achieved by the rotor at start-up is preserved by disengaging when capacitor 348 is charging, re-engaged when the next pulse of energy is given to the motor and will again disengage when completed. The entire sequence is conveniently controlled with the same signal that turns transistor 360 ON and OFF as capacitor 348 charges and discharges in the enhancement techniques of FIGS. 3 and 3A. When this is done, the signal to transistor 360 is synchronously delayed so that the mechanical linkage is optimally engaged at the same time that the energy stored in capacitor 348 is released into the motor. The feature can also be used with FIG. 3B, but its advantage is not as great because, in this case, once started, the motor stays on until target pressure is achieved.

Regardless of the method used for driving motor 221, flip flop 336 is controlled by the $A_N$ output conductor of counter 322, by an output signal of the digital window decoder 386, and by the BT conductor. The flip flop 336 is set to "1" state when the $A_N$ output of the counter 322 goes high if the BT conductor is high; and is reset by the output conductor of the decoder 386. Counter 322, in turn, is controlled by the $F_{d1}$ signal at the output of flip flop 320 and by the output of flip flop 362. Flip flop 362 is set by a $F_{d1}$ signal at the output of flip flop 320 and reset by a $B_n$ output signal of counter 364. Counter 364 defines a period of time in terms of pulses of the reference frequency $F_{r1}$ and counter 322 counts the difference frequency pulses $F_{d1}$. Since counter 364 and counter 322 are reset at the same time by an output signal of flip flop 362, counter 364 provides a measurement window of time which runs from reset time to the next reset time. The $A_N$ output conductor will remain low until the deformation of the spring 227 reaches the target value. When the counter 322 reaches the $A_N$ count within the measurement time window, flip flop 336 is set and gate 338 is disabled. At the same time, the "1" output of flip 336 is transmitted to the warning function 388 to indicate that the device is ready for an injection procedure. Flip flop 336 can be set only if the "BT" input to the "D" terminal of that flip flop is high. As will be explained with respect to FIG. 4, the BT conductor will be high if the bellows test is satisfactory. The digital code which is stored in counter 322 during a measurement time interval corresponds to the instant deformation of the energy storage spring 227. The digital pulse decoder 324, in response to the digital code in counter 322, generates input signals for the BCD counters 326, 328. For example, if the deformation of the spring which is equivalent to one pound of force on the spring provides ten cycles of differential frequency $F_{d1}$, decoder 324 will convert the code in counter 322 to a single pulse for BCD counters 326, 328. With a count of one in the counters 326, 328, the BCD decoders 330, 332 provide signals to the display 334 to display the value, one pound. Any number can be displayed with appropriate decoding by pulse decoder 324. By virtue of the display 334, the operator knows that the appropriate level of energy is stored in the spring 227 and that an injection may be initiated. The flip flop 336 remains set until an injection has been successfully completed. If the velocity test fails, a warning in 388 will issue and flip flop 336 will not be reset. Accordingly, remedial action must be taken before preparation for another injection can be started.

The power on switch 375, in the lower left portion of FIG. 3, connects positive battery potential to the input of inverter 379 through the contact segments 370 and 371, detents 232 and 233, and line 377. The contact segments 370 and 371 lie in the recesses 108 on the back plate 104 shown in FIGS. 1 and 2. When the trigger is operated, the detents 232 and 233 are disconnected from the contact segments 370 and 371; and, because the input is referenced to ground through resistor 374, the output of inverter 379 goes high. A high signal from the output of inverter 379 increments a counter in 390 to display the number of injections completed from the current bellows; and causes the "D"-type flip flop 380 to be set to the "1" state. Consequently, the "0" output of flip flop 380 goes low which disables AND gate 338. The high signal on the "1" output of flip 380 enables AND gate 382 to pass $F_{d1}$ difference frequency signals to the input of counter 384. As explained earlier herein, the difference frequency will be reduced accordingly as spring 227 comes to some predetermined value after an injection. The count which is accumulated in the counter 384 is thus representative of the time required for the bellows to be partially collapsed. The window decoder 386 evaluates the count in the counter 384 on the basis of the expected values established by IC 2. If the count is larger than the expected limits, it is probable that the output port is plugged, and if the count is smaller than the expected limits, it is probable that the output port is enlarged beyond acceptable limits. In either event, a warning signal is displayed by the warning indicator 388 and the flip flop 336 will not be reset until remedial action is taken. If the count in counter 384 is within limits, an output signal of digital decoder 386 will reset flip flop 336 and the BCD counters 326 and 328. When that occurs, the cycle to drive the motor to load energy into the spring 227 will begin again. The time required for the bellows to partially collapse is short compared to the time required for the detents 232 and 233 to again settle in the recesses 108 and reconnect positive potential to the input of inverter 379. This time relationship is positively assured if a dashpot is employed to slow the return as suggested earlier herein. When the positive potential reappears at the input of inverter 379, capacitor 376 and resistor 378, which are configured as a high-pass filter, produce a reset pulse to flip flop 380 and counter 384 in preparation for the next injection. In the event that a very large volume injection is to be performed, the time required to inject the fluid may exceed the time for the detents 232 and 233 to settle in recess 108. In that case the illustrative high-pass reset circuitry can be replaced with circuitry with appropriate delay.

FIG. 4 provides an arrangement for testing the integrity of the liquid-filled bellows 404 or any other type of fluid-filled cartridge. Inverters 400 and 402 are configured as an oscillator in which the output frequency $F_b$ is determined by the impedance across the entire bellows 404. Inverters 410 and 412 are configured as a fixed frequency oscillator having a frequency $F_{r2}$; and flip flop 420 is connected as a frequency mixer for the signals $F_{r2}$ and $F_b$. In the configuration of FIG. 4, the collapsing bellows behaves as a variable resistance; therefore, the frequency of the mixer output signal $F_{d2}$ is minimum when the bellows is full. As the bellows collapses, the impedance decreases and the differential signal $F_{d2}$ increases. The counter 422 accumulates the $F_{d2}$ signals during a measurement time interval defined by the "0" output conductor of flip flop 362 of FIG. 3, and pulse decoder and display 424 displays bellows status information. The use of the time period provided by the $D_N$ count is for purposes of illustration. In the event that a different time period is desired, additional counter outputs and flip flops are provided. The arrangements of 424 evaluate the interval count in counter 422 on the basis of the IC set 3 information which defines a range or window of acceptable values. If the count falls within the range of acceptable values, a high BT signal will be generated and flip flop is set on occurrence of the next succeeding $A_N$ signal from counter 322. However, if the serum within the bellows has excessive voids, clots or an incorrect consistency for some other reason, the $F_b$ frequency will fall outside the acceptable range and the count in 422 will fall outside the preselected window of performance.

It should be noted that fluid may be used as a dielectric material in an alternative embodiment in which a variable capacitance determines the frequency $F_b$. In that embodiment the variable bellows is located at the position of the capacitor 408 and a fixed resistor placed at the position 404 in FIG. 4. In this case, the two ends of the bellows form the capacitor plates and the serum fluid is the dielectric material. As the length of the bellows decreases, the capacitance increases and the frequency $F_b$ decreases.

FIGS. 5A to 5D show a needle-type hypodermic injector in accordance with my invention in various stages in the use of the injector. The injector of FIG. 5A comprises a bellows 500 sealed with end cap and ram 510; a front housing 503; a rear housing 502; a pressure piston 501.; a needle output port 508 with a flange 511; a bellows-shaped needle sheath 504; and a removable cap 507. FIG. 5A illustrates a fresh injector prior to use. As in the injector embodiment of FIGS. 1 and 2, the support guide rings 116 of those figures may be employed in the embodiment of FIGS. 5A to 5D. The bellows 500 may contain a liquid serum or a lyophilized (freeze dried) vaccine. In the latter case, a liquid which is stored in the sheath bellows 504 is driven into the bellows 500 as described below herein. The bellows 500, the rear housing 502 and the front housing 503 all may be fabricated of clear plastic material so that the operator can observe whether or not blood is drawn into the bellows 500 when the pressure piston is slightly withdrawn.

The breakaway seal 512 and the cap 507 are removed to permit the operator to depress housing 502. The need to remove the cap 507 may be eliminated if the cap 507 is made of a self-sealing material, e.g., pure latex rubber. Typically, the thumb is placed on the pressure piston 501 and index finger and the adjacent finger are placed on the flange 511. The resistance of the sheath bellows 504 is sufficient to cause the bellows to expand after use; however, the resistance of the bellows 504 is small compared to the force required to compress the liquid bellows 500 to eject the liquid through the needle output port. Therefore, as pressure is applied between the flange 511 and the pressure piston 501, the sheath bellows will begin to collapse and needle exposure will begin. As the sheath bellows is collapsed, the right-hand side 520 of needle 506 will puncture the membrane separating sheath bellows 504 and serum bellows 500. As compression continues, the liquid residing in sheath bellows 504 is forced into serum bellows 500 to form the fluid state of the desired serum. Ultimately, needle flange 505 will engage the surface 514 therein, after removal of breakaway seal 513. Continued pressure will force the serum in 500 to be expelled through the exit port of needle 506, said serum being unable to re-enter 504 because it has collapsed to zero internal volume. A foam ring 516 positioned on the right side of flange 505 serves as a cushion to prevent flange 505 from opening the membrane to a greater extent than that of puncture point 520. The membrane in 500 also can be made of self-sealing latex diaphragm material which will tend to hold the needle in place after the injection is completed and the sheath is again extended to cover the needle. The first intermediate state of the injector is illustrated in FIG. 5B.

In cases where the serum is stored in bellows 500 in a liquid state, the bellows 504 can be replaced with a simple coil spring. However, if as suggested earlier herein, the vaccine is stored in the lyophilized state, the fluid required to turn the vaccine to the liquid state is stored in the bellows 504. In this latter case, the liquid in bellows 504 is forced into bellows 500 through a hole in the membrane of the bellows 500 which is breached when the bellows 504 is first compressed to begin exposure of needle 506.

After the needle is inserted into the injection site, the breakaway seal 513 is removed and pressure is applied between the pressure piston 501 and the flange 511 to collapse the liquid bellows 500 and eject fluid through the output ports into the injection site. The state of the injector after depletion of the injection fluid is illustrated in FIG. 5C. As shown in FIG. 5E, a sawtooth pattern 518 on the outer surface of the pressure piston 501 and a single sawtooth 517 on the inner surface of the rear housing 502 permit the pressure piston 501 to be advanced into the member 502 and thus compress the bellows 500. However, the cooperation of 517 and 518 prohibits withdrawal of the piston 501 after engagement of 517 and 518. As an option, the end of the ram 510 is shaped to strike and crush the end 520 of the needle 506 when the bellows 500 is fully collapsed. This will further assure that the needle injector cannot be reused and will tend to retain the needle in engagement with the bellows 500 when the sheath bellows 504 and the sheath 503 are extended to cover the needle.

After the needle is removed from the subject and pressure between 501 and 511 is removed, the bellows 504 expands as shown in FIG. 5D. As is seen in FIG. 5D, when the needle sheath bellows 504 extends to its full length, the needle 506 is withdrawn from the needle guide 508. This occurs because, in preparation for the injection, end 520 of needle 506 penetrated the membrane to breach the serum chamber. Because the needle guide opening 508 is small compared to the trap opening 509, it is difficult if not impossible to again collapse the bellows 504 without the end of the needle 506 hitting the end wall 515 of the trap section 509. The tendency of the needle to hit the wall 515 can be enhanced by imparting a small bend in the needle 506 prior to initial installation into the guide opening 508.

Figure 7:
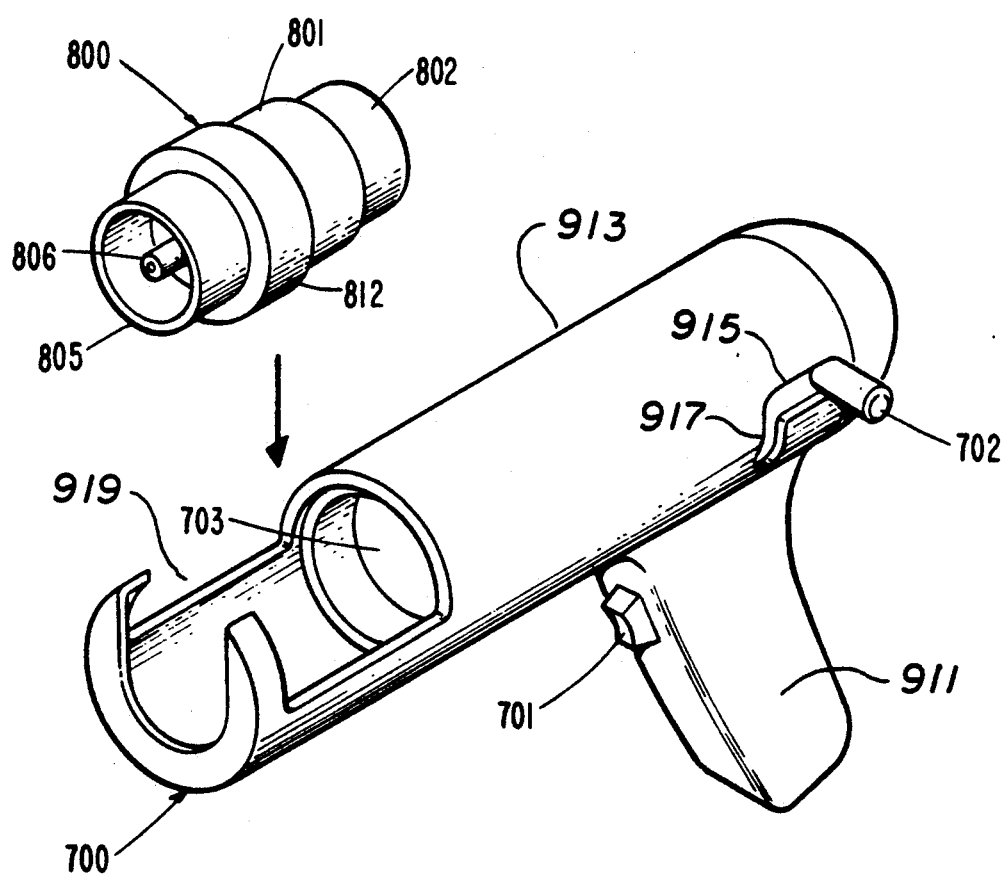
FIG. 7 is a pictorial view of an alternative embodiment of a jet injector in accordance with my invention.

FIG. 7 shows an alternative embodiment of a jet injector system in which the serum for each and every injection is individually contained in its own collapsible cartridge. A dispenser 700 includes a handle 911 from the forward end of which extends a trigger 701. A muzzle 913 includes at its rearward section a lever 702 extending laterally through a longitudinal slot 915 in muzzle 913 which terminates at its forward end in a downward extending portion 917. Dispenser 700 includes at its forward end a receptacle or opening 919 for receiving a cartridge 800 holding a serum for injection into a recipient. Dispenser 700 includes a piston or ram 703 for acting on cartridge 800 to effect an injection. Cartridge 800 is described below and shown in FIGS. 8A and 8B.

For illustrative purposes, the cartridge 800 shown in FIG. 7 is grossly oversized, wherein a normal injection requires from ¼ to 1 cc of serum (from about 0.031 to 0.061 in³) and the actual cartridge size is commensurate with that volume. Since the system of FIG. 7 can be proportioned to handle single-shot or multiple-shot cartridges, the smaller size is also true for the magazine embodiment of FIGS. 7A and 7B, that is, the illustrative magazine is many times larger than that needed for the N cartridges shown in the figures. For a single-shot arrangement, the lever 702 is drawn to the rear to permit removal of a used cartridge from receptacle 919 and a fresh cartridge installed. After a fresh cartridge is installed, the lever 702 is moved forward, to the left in FIG. 7.

Figure 7A:
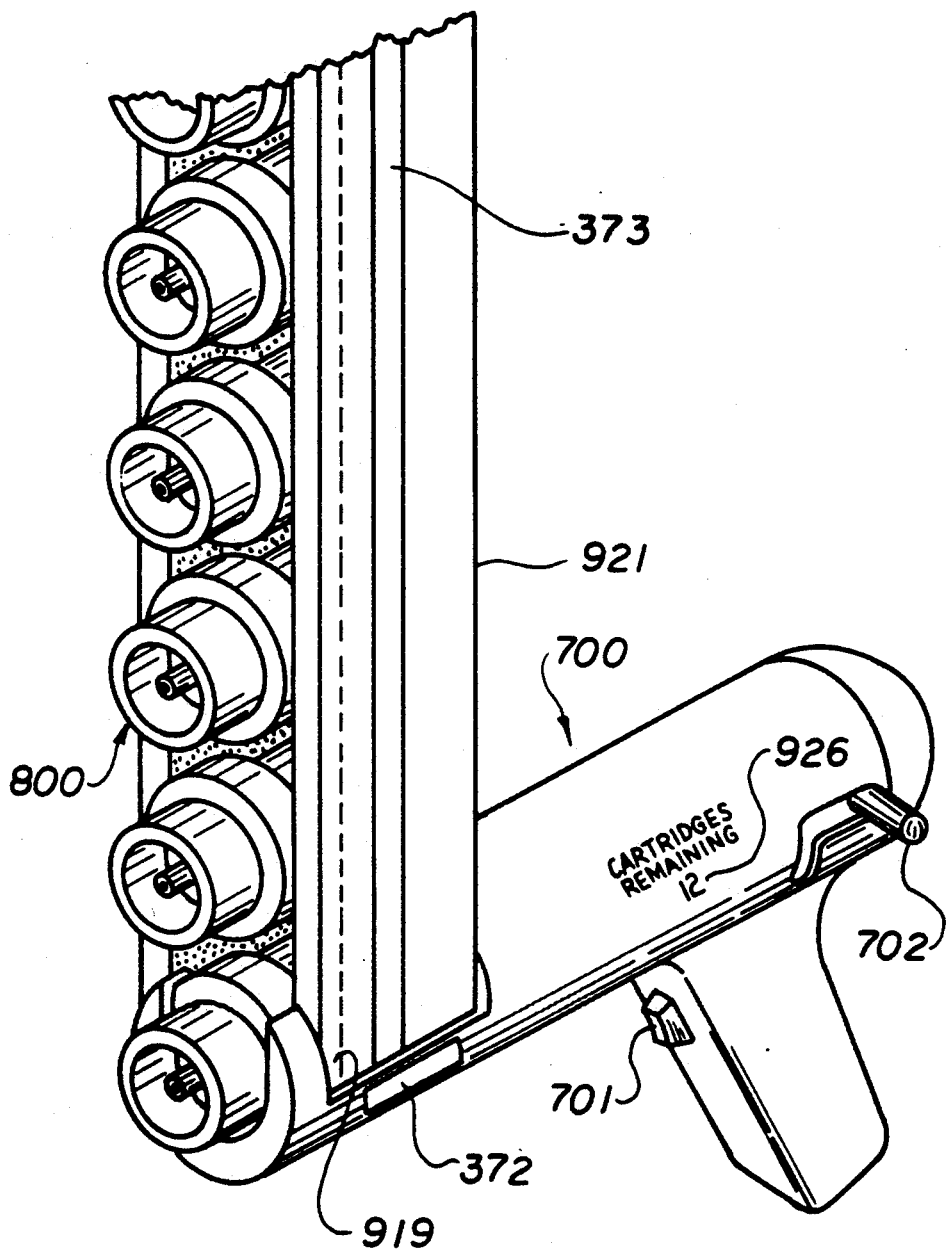
FIG. 7A shows an oversized perspective view of the injector of FIG. 7 of a fresh magazine with N unused injections positioned in the dispenser.
Figure 7B:
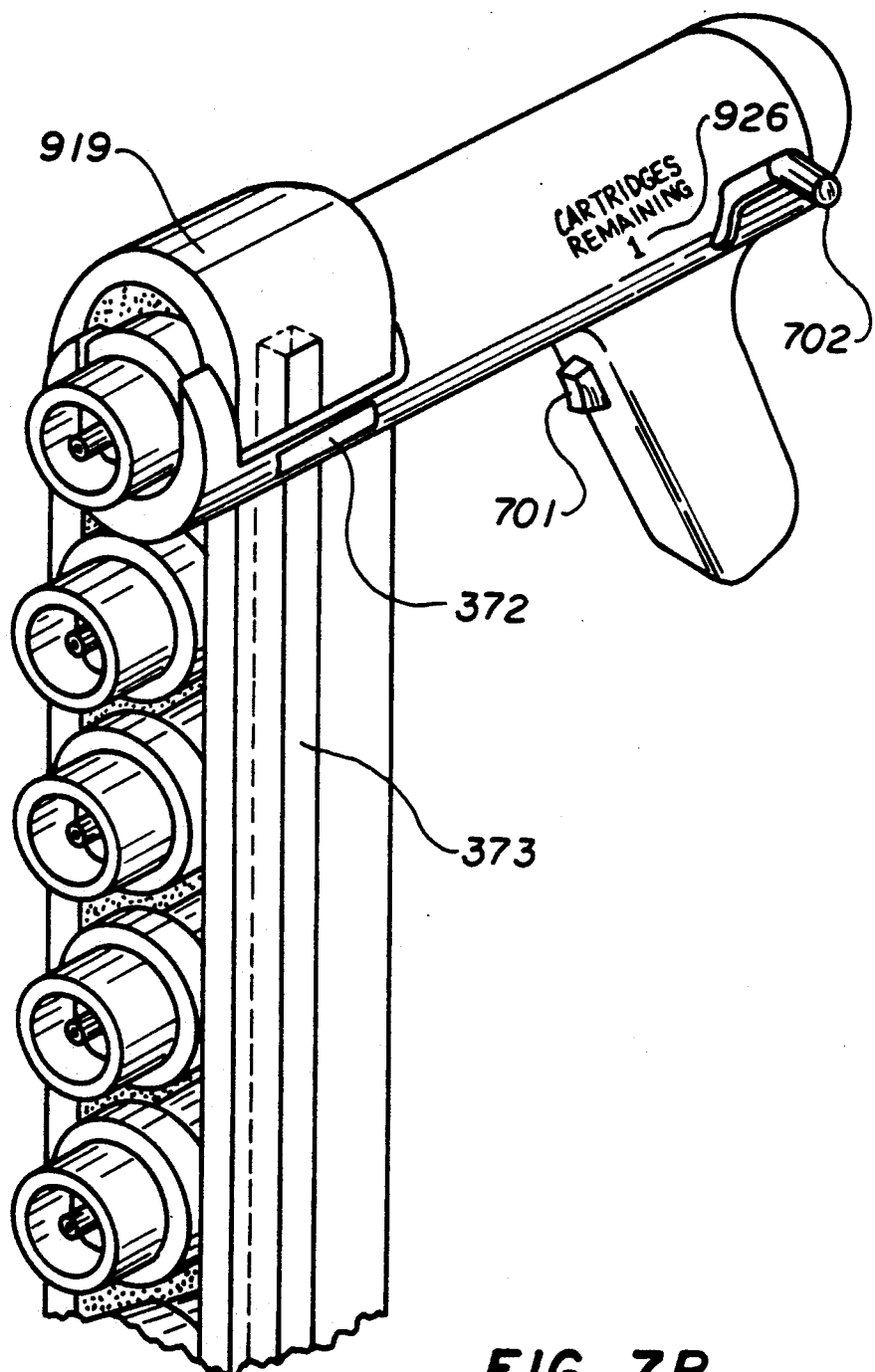
FIG. 7B shows the oversized magazine illustrated in FIG. 7A with the N-1 injections having been used.

With regard to the magazine embodiment of FIGS. 7A and 7B in which the N cartridges 800 are serially introduced into system 700, which is shown identical to that in FIG. 7, many magazine configurations are possible for sequential loading into and out of the injection chamber. For example, much in the manner of a modern pistol with a linear magazine containing N bullets or, the revolver-type weapon in which the bullets rotate into the chamber or, as shown in the oversized preferred embodiment of FIGS. 7A and 7B, there is shown the entire magazine 921 which is simply detented through opening 919 in the injector chamber as each new injection occurs. In this latter arrangement, the cartridges are not extracted at the completion of each injection, but simply remain in magazine 921. This feature is especially important for the prevention of unsafe relittering at the scene of mass immunization programs such as the military or activities of the World Health Organization in their worldwide efforts with disease control. Other methods of collection and storing the used cartridges are also possible, for example, a magazine that has an evacuated volume equal to that of the loaded cartridges, and into which the used cartridges will drop at the conclusion of an injection.

A manual advance for the magazine can be implemented with lever 702 or an automatic advance is realized with a spring configured ratchet assembly that is "wound up" when magazine 921 is slipped into the bottom opening of the dispenser 700 and urged upward until latched into the initial position for the injection sequence. Since the system is electrical in nature, a motor advance is the most convenient of all; however, power conservation for a multitude of high pressure injections has a higher priority in many applications. As discussed earlier, any suitable driving force can be utilized to drive pressure piston 703 forward to collapse the serum chamber 804 in cartridge 800 (as explained below) when said cartridge appears at the injection site.

Switch 375 is basically the ON-OFF switch for system power. The manner in which the power is provided can be carried out in a number of ways, wherein the one selected is normally dictated by the application and/or user preference. Three ways are described below.

Referring to FIG. 3 for one such way, switch 375 is simply turned ON, after which flip flop 336 automatically enables gate 338 and turns ON motor 221; when target pressure is detected, flip flop 336 disables gate 338. This cycle continues until a system failure occurs or the injection capability is depleted. In a single or multiple cartridge system, the detent action of contacts 232, 233 is provided as part of the trigger mechanism 701 in FIGS. 7, 7A and 7B.

Figure 3C:
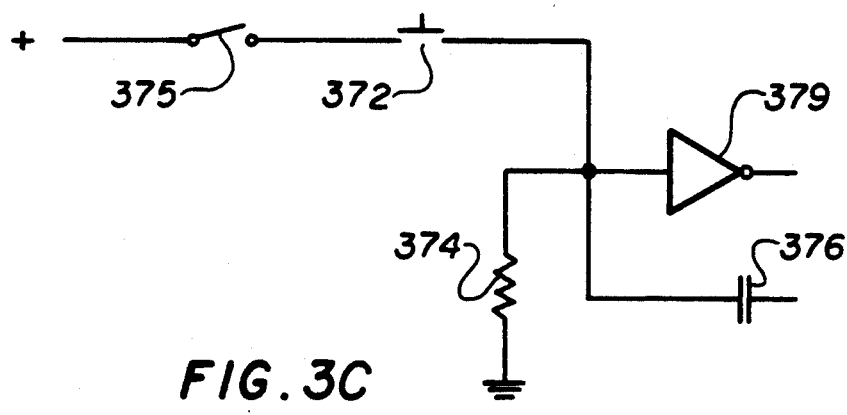
FIG. 3C is an alternate embodiment of the power switch shown in FIG. 3.

Turning to FIGS. 7A and 7B for another embodiment, momentary switch 372 in FIG. 3C replaces the latching contacts 232, 233. Switch 375 still provides primary power to the system, but switch 372 is a momentary switch which is "open" until the magazine is securely positioned in the dispenser, after which switch 372 closes as it engages the first cartridge through slot 373 in the wall of magazine 921. Thereafter, the injector automatically becomes active and develops the required pressure for the next injection. In some applications, and as shown in FIG. 3C, switch 375 is only activated when a live cartridge is located on the injection chamber, wherein switch 372 detects the presence of pressure piston 802 (FIG. 7) if the cartridge is full but has no such interface if the cartridge is expelled. Because of the void between cartridges, it is also deactivated between "shots". These features are most useful for situations where a partially used magazine is inserted into the dispenser.

A MANUAL/AUTO select is provided in a third embodiment, wherein in the manual mode switch 372 is depressed by the user rather than by the cartridge in the AUTO mode. However, the AUTO mode is also provided, as described in the preceding paragraph.

When the magazine and cartridge embodiment is used, counter and display function 390 will electronically measure and display the number (shown as 926 in FIGS. 7A and 7B) of "live" cartridges actually found in the magazine. The counter and display number will then proceed with a countdown to zero as the cartridges are used. Again, this feature is important for situations where a magazine is removed and then returned to the dispenser for a later round of injections.

It is clear that in the magazine-type system, the expended cartridges can be safely disposed of; however, for purposes of economy in certain situations, the magazine can be ruggedly built for multiple long term use, in which case the entire magazine can be returned to a center for disease control, sterilized and reused in whole or in part. In one such embodiment, the cartridges themselves are reusable, but the exit nozzle is removed and replaced in the same manner as described for the multiple-dose cartridge of FIGS. 1 and 2. If the magazine is reusable, a preferred embodiment of this feature has the cartridge counter, its processor, display and a power source ideally located right in the magazine. With this embodiment, no count initialization is necessary because it simply detects the live cartridges found in the magazine on a real time basis whether the magazine is in the dispenser or not. In fact, this technique is useful for other magazine-oriented applications such as pistols, shotguns, rifles and automatic or semi-automatic weapons of any type. For such a system, a low battery warning would be used with the independent counter system as well. A specially designed version of the reluctance transducer and processor described for FIG. 3 is ideally suited for this embodiment.

Finally, it is noted that a dispenser similar to that of FIG. 7 can be used for the needle oriented cartridges of FIG. 5. Further, if the FIG. 5 cartridge is designed into the magazine structure of the FIG. 7A dispenser, then N needle-type cartridges can be administered in much the same way as the jet injector, but with greater efficiency and speed than that of the individual cartridges, and with even less risk to the population because the entire magazine remains under the watchful eye of the immunization team. As in the case of the FIG. 5 embodiment, the jet injector of FIGS. 7 and 8 can be fabricated of clear plastic material so that the operator can observe if the needle has penetrated a blood vessel after insertion, but prior to expelling the fluid. This is possible by virtue of an automatic micro-withdrawal of the pressure piston under the influence of the monitoring and control sequence of the electrically driven system.

Figure 8A:
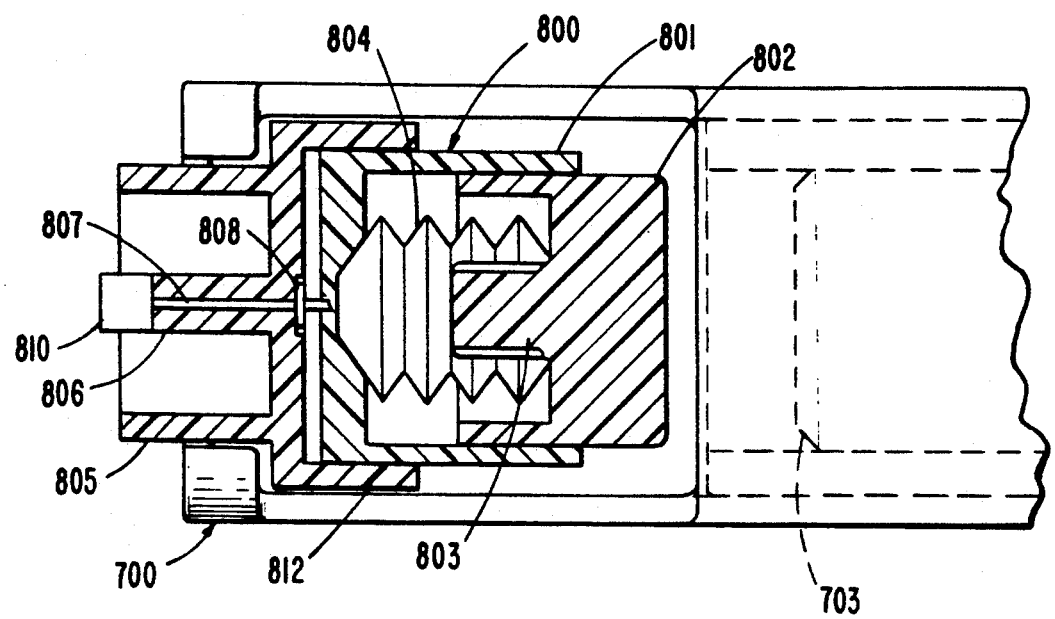
FIG. 8A shows a side, partial view of the jet injector system illustrated in FIG. 7 with a fresh cartridge installed therein.
Figure 8B:
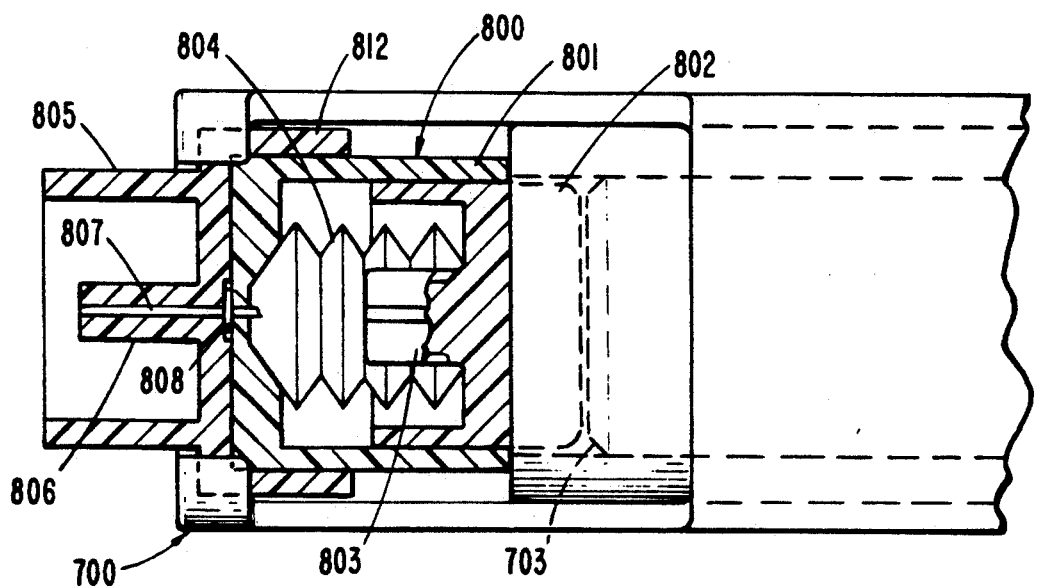
FIG. 8B shows a side, partial view of the jet injector system of FIGS. 7 in which the cartridge has been breached.

The cartridge 800 is shown in detail in FIGS. 8A and 8B. Cartridge 800 comprises a sealed serum bellows 804 with a ram 803; a rear housing 801; a pressure piston 802; a front housing 812, which comprises a guard ring 805 and a jet output port 807 with a flange 808; and removable cap 810. FIG. 8A illustrates a fresh injector installed in the system of FIGS. 7, 7A or 7B prior to breaching the seal of the serum bellows 804.

FIG. 8B illustrates the arrangements of FIG. 8A after the lever 702 of FIG. 7 is moved forward to breach the seal of the bellows 804 and to bring the injector piston 703 in position to drive the pressure piston 802 forward to collapse the bellows 804.

The illustrative embodiments of my invention which are disclosed herein are but representative of my invention and many changes in form and function can be made without departing from the spirit and scope of my invention.

The embodiments of the invention in which an exclusive property or privilege is claimed are defined as follows:

1. A hypodermic fluid dispenser for receiving a sequence of collapsible bodies, each forming a chamber for holding a fluid, said dispenser comprising:
   pressure application means for sequentially applying pressure to a sequential supply of said bodies to collapse said bodies in turn, to force fluid held in said chamber therefrom, said pressure application means including:
   repetitively charged storage means for storing electrical energy of relatively high value, said storage means being connectable to a primary source of electrical energy, the energy of said storage means being higher than the instantaneous energy available from said primary source;
   resilient means sequentially connectable to received collapsible bodies for expanding from a compressed state to collapse the bodies;
   motor means for advancing a ram means to compress said resilient means; and
   a source of electrical pulses having relatively high energy and short duration, said source being energized by said repetitively charged storage means and transmitting relatively high energy, short duration pulses to energize said motor.

2. A hypodermic fluid dispenser for receiving one or more collapsible bodies, each body including a chamber for holding a fluid, and for injecting said fluid, said dispenser comprising:
   insertion means for inserting sequentially one or more of said bodies into said dispenser;
   pressure application means for sequentially applying pressure to each of said one or more bodies to collapse said bodies in turn, to force hypodermic fluid from the respective chambers, said pressure application means including:
   resilient means sequentially connectable from an energized state to said received one or more collapsible bodies for collapsing the one or more bodies in response to the application of force of sufficient magnitude and duration to said resilient means;
   motor means for energizing ram means to compress said resilient means; and
   a source of electrical energy of sufficient magnitude and duration to energize said motor to energize ram means to compress said resilient means to collapse the bodies to inject said fluid.

3. A hypodermic fluid dispenser according to claim 2 wherein said insertion means further expels said one or more bodies into and out of said dispenser.

4. The invention according to claim 2 wherein said insertion means includes a magazine for storing said bodies, and said sequence contains N collapsible bodies stored in said magazine.

5. The invention according to claim 4 wherein said insertion means includes a magazine for holding N bodies and includes an initially vacant body holding part, and each of the N collapsible bodies is expelled into said initially vacated part at the completion of each of the injections 6. The invention according to claim 4 wherein said insertion means includes a magazine for holding N bodies, and said sequence of N collapsible bodies remain at their initial location in said magazine for all N injections, and means for moving said magazine through the dispenser for collapsing each cartridge per injection.

7. The invention according to claim 6 and further including said magazine wherein the N collapsible bodies are a permanent part of said magazine.

8. The invention according to claim 4 wherein said collapsible body in said dispenser further comprises output means for discharging fluid from said body when said body is at least partially collapsed.

9. The invention according to claim 8 wherein said collapsible body in said dispenser comprises guard means near said output means for preventing contact between a patient's skin and said output means.

10. The invention according to claim 9 wherein said guard means comprises a guard ring.

11. The invention according to claim 9 wherein said guard means has an interrupted pattern to prevent sliding between the dispenser and the skin.

12. The invention according to claim 8 wherein said body in said fluid dispenser further includes outflow port means for defining a discharge from said body having enclosed collapsible bellows.

13. A hypodermic fluid dispenser in accordance with claim 4 and further including:
   means for counting the number of bodies remaining in said magazine during a series of injections, and for generating output signals in accordance with the count; and
   means responsive to output signals of said counting means for displaying the number of bodies remaining in said magazine.

14. The invention according to claim 4 wherein said dispenser further comprises a disposable and replaceable exit nozzle for discharging fluid from the chambers of said collapsible bodies;
   wherein said resilient means apply sufficient pressure to said body to discharge an injection fluid from said chamber and through said disposable nozzle.

15. A hypodermic fluid dispenser in accordance with claim 2 wherein said dispenser is compact and hand-held during operation.

16. A hypodermic fluid dispenser in accordance with claim 2 wherein said motor means is operably connectable to a small battery source for producing said source of electrical energy for energizing said ram means to compress said resilient means.

17. A hypodermic fluid dispenser in accordance with claim 16 wherein said motor means is energizable from a low capacity energy source to supply an intermediate source of stored energy, and has engaging/disengaging means to preserve rotor momentum during intervals of resupplying the intermediate energy source.

18. A hypodermic fluid dispenser in accordance with claim 16 wherein the time period for compressing said resilient means increases as the motor means drive capability decreases and/or the capacity of said electrical energy source decreases.

19. The invention according to claim 2 wherein said resilient means is spring means.

20. The invention according to claim 2 and further including monitoring means for monitoring the deformation of said resilient means to terminate the energy to said motor means when said deformation reaches a predetermined value, said monitoring means including a source of reference pulse signals having a first pulse rate, and a source of monitor pulse signals said source having a means for modifying the monitor pulse rate in accordance with the magnitude of the deformation of said resilient means.

21. A hypodermic fluid dispenser according to claim 20 wherein said source of monitor pulse signals comprises a variable inductance for setting the pulse rate of said monitor pulse signals, and wherein said inductance is varied as a function of the deformation of said resilient means.

22. A hypodermic fluid dispenser according to claim 20 wherein said dispenser includes means for displaying values which define the magnitude of deformation and the value of the stored mechanical energy of said resilient means.

23. A hypodermic fluid dispensing system having a hypodermic fluid dispenser and at least one collapsible body, said dispenser receiving a sequence of said collapsible bodies, each body having a chamber for holding a fluid and each body containing a hypodermic needle means, said dispensing system comprising:
 insertion means for inserting sequentially said bodies into said dispenser;
 sheath means includes with each body for covering said needle means before and after collapse of each of said bodies in said dispenser; and
 pressure application means for sequentially applying pressure to the sequential supply of said bodies to collapse said bodies in turn.

24. The invention according to claim 23 further comprising:
 means for uncovering said needle means by said sheath means to expose said needle means and for moving said sheath means into communication with said body; said pressure application means being actuable to emit pressure to collapse said sheath means covering the needle means to extend said needle means to force fluid held in said chamber through said needle means.

25. The invention according to claim 23 in which said sheath means is bellows shaped.

26. The invention according to claim 23 wherein said means for applying pressure is deactuable to cause said sheath means to expand, to retract said needle means into said sheath means.

27. The invention according to claim 26 and further comprising means to prevent said needle means from being extended from said dispenser after said needle means had made an injection.

28. The invention according to claim 23 and further including:
 resilient means sequentially connectable from an energized state to collapse the ram means to compress said collapsible bodies.

29. The invention according to claim 28 and further including:
 motor means for advancing said ram means; and
 a source of energy of sufficient magnitude and duration to energize said motor means to energize said ram means to produce the desired injection upon deenergization of said motor means.

30. The invention according to claim 28 wherein said body in said dispenser is formed of transparent material.

31. The invention according to claim 23 wherein said needle means is located in a second holding means of said collapsible body, said second holding means holding a second, non-liquid serum ingredient, and positioned to penetrate the other serum ingredient holder, said penetration occurring to cause said first and second ingredients being brought together in response to pressure applied to said body and wherein said sheath contains a liquid for converting the non-liquid serum in second holding means to a liquid serum, and wherein during operation of the dispense said needle means brings said sheath into communication with said second body to cause the liquid serum to enter said second body to produce said liquid serum when said sheath is collapsed.

32. Apparatus according to claim 23 and further including means within said body in said dispenser to prevent needle means form being operable after the needle means has been used.

33. A hypodermic fluid dispenser for receiving one or more collapsible cartridges, each cartridge including a chamber for holding a fluid, and for injecting said fluid, said dispenser comprising:
 insertion means for inserting sequentially one or more of said cartridges into said dispenser; and
 pressure application means for sequentially applying pressure to each of said one or more cartridges to collapse said cartridges in turn, to force hypodermic fluid from the respective chambers, said pressure application means including:
 resilient means sequentially connectable from an energized state to said received one or more collapsible cartridges for collapsing the one or more cartridges in response to the application of force of sufficient magnitude and duration to said resilient means;
 motor means for energizing ram means to compress said resilient means; and
 power switch means for selectively connecting a source of electrical energy of sufficient magnitude and duration to energize said motor to said resilient means to collapse the cartridges to inject said fluid.

34. A hypodermic fluid dispenser according to claim 33 and further including manually actuable means for actuating said power switch means for selectively connecting one source of electrical energy to said motor means to achieve the pressure needed to collapse said cartridges, and for deactuating said manually actuable means when said pressure to collapse said cartridges is attained.

35. A hypodermic fluid dispenser according to claim 33 and further including means actuable by said cartridges for actuating said power switch means to connect the source of electrical energy to said motor means.

36. A hypodermic fluid dispensing system having a hypodermic fluid dispenser and at least one collapsible body, said dispenser receiving one or more of said collapsible bodies, each body including a chamber for holding a fluid, and for injecting said fluid, said dispensing system comprising:
 insertion means for inserting sequentially one or more of said bodies into said dispenser;
 pressure application means for sequentially applying pressure to each of said one or more bodies to collapse said bodies in turn, to force hypodermic fluid from the respective chambers, said pressure application means including:
 resilient means sequentially connectable from an energized sate to said received one or more collapsible bodies for collapsing the one or more bodies in response to the application of force of sufficient magnitude and duration to said resilient means;

motor means for energizing ram means to compress said resilient means; and a source of electrical energy of sufficient magnitude and duration to energize said motor to energize said ram means to compress said resilient means to collapse the bodies to inject said fluid.

* * * * *